US00PP34623P3

(12) United States Plant Patent
Brotzman et al.

(10) Patent No.: US PP34,623 P3
(45) Date of Patent: Oct. 4, 2022

(54) SYCAMORE PLANT NAMED 'DRABROT'

(50) Latin Name: *Platanus occidentalis*
Varietal Denomination: DRABROT

(71) Applicants: Timothy C. Brotzman, Madison, OH (US); Thomas M. Draves, Darien, NY (US)

(72) Inventors: Timothy C. Brotzman, Madison, OH (US); Thomas M. Draves, Darien, NY (US)

( * ) Notice: Subject to any disclaimer, the term of this patent is extended or adjusted under 35 U.S.C. 154(b) by 60 days.

(21) Appl. No.: 17/135,807

(22) Filed: Dec. 28, 2020

(65) Prior Publication Data

US 2021/0204458 P1 Jul. 1, 2021

Related U.S. Application Data

(60) Provisional application No. 62/974,918, filed on Dec. 31, 2019.

(51) Int. Cl.
*A01H 5/00* (2018.01)
*A01H 6/00* (2018.01)
*A01H 5/04* (2018.01)

(52) U.S. Cl.
USPC ..... Plt./216
CPC ..... *A01H 6/00* (2018.05); *A01H 5/04* (2013.01)

(58) Field of Classification Search
USPC ..... Plt./216
CPC ..... A01H 6/00; A01H 5/00; A01H 5/04
See application file for complete search history.

*Primary Examiner* — Keith O. Robinson

(57) ABSTRACT

A new variety of *Platanus occidentalis* named 'DRABROT' which is characterized by a contorted, semi-weeping branch habit and dark green, disease-free leaves. In combination, these characteristics distinguish 'DRABROT' from all other cultivars known to the inventors.

2 Drawing Sheets

Genus: *Platanus*.
Species: *occidentalis*.
Denomination: 'DRABROT'.

BACKGROUND OF THE INVENTION

The present invention relates to a new and distinct cultivar of *Platanus occidentalis* (American Sycamore or American Planetree) which is grown as a large ornamental tree for use in parks and landscape. The new cultivar is known botanically as *Platanus occidentalis* and will be referred to hereinafter by the cultivar name 'DRABROT'.

The 'DRABROT' variety was found by Thomas M. Draves, an ISA Certified Arborist, as a free-standing specimen tree incorporated into the landscape of a residence in Darien, N.Y. and was recognized by him as unique for its contorted habit and semi-weeping branches. There is no evidence of 'DRABROT' arising as a mutation from any known form of *Platanus*, and therefore it is assumed to be a seedling of *Platanus occidentalis*, planted in its current location at least 60 years ago.

The 'DRABROT' variety is the only variant of American Sycamore we are aware of that displays this form when compared to the following commercial selections: *Platanus occidentalis* 'Yellow Sycamore' U.S. Plant Pat. No. 5,359 with an arboreal form typical of the species but slower growth and yellow leaves; *Platanus occidentalis* 'Grenickle' (not patented) SILVERWOOD™ Sycamore, with both height and width reaching 75-100', bark white. The majority of commercially produced *Platanus* are forms of the hybrid *Platanus* x *acerifolia* (*Platanus occidentalis* x *Platanus orientalis*), commonly known as London Planetree, none of which have the unique form of the 'DRABROT' selection, and as noted in *The Tree Book*, by Dirr & Warren, Timber Press 2019, are represented by the following four, nonpatented cultivars: *Platanus* x *acerifolia* 'Bloodgood' (70' tall×50' wide); *Platanus* x *acerifolia* 'Columbia' (70' tall×50' wide, USDA hardiness zone 6), *Platanus* x *acerifolia* 'Morton Circle' (EXCLAMATION!™ London Planetree) (60' tall×30' wide); and *Platanus* x *acerifolia* 'Suttneri' (60' tall×45' wide, white and green variegated leaves, bark almost pure white).

The original tree is approximately 35' tall by 48' wide, and has developed two separate trunks with diameters of 10" and 12". Although we have reproduced 'DRABROT' with two or more primary stems, most commercial applications utilize trees with only one, therefore, our observations and illustrations for the purpose of this declaration have focused on trees with one trunk. Specifically, the oldest plant available to us, produced from the original, is a 17-year old single-stem specimen in [The Draves Arboretum] an arboretum, currently measuring 16' tall×21' wide, and that has a diameter of 6" at a point 12" above the ground.

ASEXUAL PROPAGATION OF THE INVENTION

'DRABROT' was first asexually propagated by Tim Brotzman, co-inventor, in summer of 2003 in Madison, Ohio. Asexual propagation has been accomplished using softwood cuttings and by budding onto seedling rootstock of *Platanus occidentalis* (not patented). Since that time, under careful observation, the distinguishing characteristics of 'DRABROT' have been determined stable and uniform, and to reproduce true to type in successive generations of asexual propagation.

DESCRIPTION OF THE INVENTION

Using observations collected from 17-year-old trees growing at [Brotzman's Nursery, Inc.] a nursery in Madison, Ohio and at [The Draves Arboretum] an arboretum in Darien, N.Y., as well as the mother tree, we have identified traits which in combination set 'DRABROT' apart from all other existing varieties of *Platanus* known to the inventors. 'DRABROT' has not been tested under all possible conditions and phenotypic differences may be observed with variations in environmental, climatic, and cultural conditions. The distinguishing characteristics of 'DRABROT' are as follows:

1. 'DRABROT' exhibits a contorted, semi-weeping branch habit.
2. 'DRABROT' lacks strong apical dominance
3. The leaves of 'DRABROT' are dark green and deciduous.
4. The leaves of 'DRABROT' have shown high degree of resistance to Leaf Anthracnose (*Apiognomonia veneta*) and Powdery Mildew (*Erysiphe platani*) in both Madison, Ohio and Darien, N.Y.
5. When grown as a single stem tree 'DRABROT' probably has a mature height and width of less than 35'×40'.
6. The mature trunk of 'DRABROT' has exfoliating bark, revealing a broken pattern of green-grayed-white colored patches.
7. 'DRABROT' is hardy at least to USDA Zone 5B.

BOTANICAL DESCRIPTION

Note: All references to color are using The *R.H.S. Colour Chart*, published by The Royal Horticultural Society, London, England 1966.

Parentage: Originated as a spontaneous seedling of American Sycamore, *Platanus occidentalis*.

Hardiness: USDA Hardiness Zone 5b.

Growth rate: Slow compared to the specie and hybrids. When propagated by chip budding, 1-yr whips of 'DRABROT' averaged 44.2" in height and 0.313" diameter, compared to *Platanus* x *acerifolia* 'Morton Circle' which averaged 72.4" and 0.813" at the same age. Three-year old 'DRABROT' exhibited the following averages: 27" annual lateral branch length; 0.25" lateral branch diameter; 3.0-3.5" internodal spacing; 33" annual vertical growth; overall total plant height of 114" and diameter of 1.35" when measured 6" above the ground. This compares to three-year-old *Platanus occidentalis* with averages of: 36" annual lateral growth; 0.225" lateral branch diameter; 4.0-4.5" internodal spacing; 72" vertical growth; overall plant height of 192" and diameter of 2.55" under field conditions in Madison, Ohio.

Form/branch habit: From a short central stem, rather than producing a dominant central leader, multiple primary branches randomly arch outward radially at angles of 35° to 70° (degrees) from vertical. As these branches elongate, they contort and the tips may flatten horizontally or droop as much as 120° to 160° from vertical, yielding an umbrella-shaped crown with an interwoven, dense, semi-weeping habit, the combination of which might make this selection slightly more vulnerable to snow and ice load than is typical of this specie.

Bark: The bark on the trunk of young trees is smooth, tight and dark, (Greyed-Green Group 195-A), with age developing lighter colored exfoliating plates (Greyed-Green Group 195-C to Greyed-Green Group 195-A) until finally on old plants nearly all white (White Group 155-C).

Leaves: Deciduous. Arranged alternately on stems, simple, with 3-5 lobes and toothed margins, palmate venation. Thick, generally tatter resistant leaf blade to 8 inches or more wide and 6-7 inches long, held horizontally to slightly pendant. Tip is acute, base of older leaves typically cuneate. Newly emerged and young leaves, until reaching full size, have an unusual basal flap for which there is not a recognized, specific taxonomic term. Proportional to the size of the leaf and up to 1" wide and 0.5" long and not attached to the petiole, unlobed, auriculate and moderately toothed perhaps best described as a modified blade stipule or irregular peltation. As the leaf matures this feature disappears, becoming cuneate. Leaf color dark green above (Green Group 137-A), lighter below (Yellow-Green Group 147-B). Upper surface of leaf smooth, underside slightly hairy, especially on the veins. Hair easily loosened and can cause eye/nasal irritation. Leaves slightly aromatic when crushed, not considered unpleasant. Petiole 2-4" long, depending on vigor and location on the tree, slightly flattened perpendicular to the leaf blade. Color variable: on young leaves, light green above and below (Yellow-Green Group 152-D) changing to light brown above (Grey-Orange Group 174-A) with age. The combination of large leaves, long petioles and dense branch habit create a specimen tree that gives an appearance of 100% foliation.

Stipules: Typical of the species, 'DRABROT' produces stipules around the nodes from which leaves emerge. Producing a stipular collar up to 0.5" wide and 1" across, they are completely attached and encircle the twig except are lobed and detached directly over the petiole. Color Green Group 137-D. Stipules gradually dry and disappear from twigs as they age.

Twigs/buds: The conical vegetative buds are dark, (Greyed-Orange Group 166-A) up to 0.25" long×0.20" wide, and only observed during the dormant season after leaf drop has occurred. During the growing season, buds are hidden and completely enclosed within the swollen, hollow base of the leaf petiole. New growth (twigs) are circular to oval in shape with faint longitudinal ribbing, Grey-Orange Group 165-A, darkening on larger (1"+ diameter), smooth branches (Grey-Green Group 197-B to Greyed-Green Group-A).

Flowers/fruit: As for the species, male and female flowers, not showy, are borne in separate, drooping, ball-like heads. The female heads of flowers develop into 1" diameter globose heads of seeds. The styles from the flowers extend from the ends of the seeds in the fruits, but bristles, such as are present in the fruits of London Planetree, are absent. Fruit color is Grey-Orange Group 164-C. Flower buds have not been observed or described for the purpose of this specification.

DESCRIPTION OF THE DRAWINGS

The accompanying color drawing, labeled

The accompanying color drawing, labeled

Figure 1:
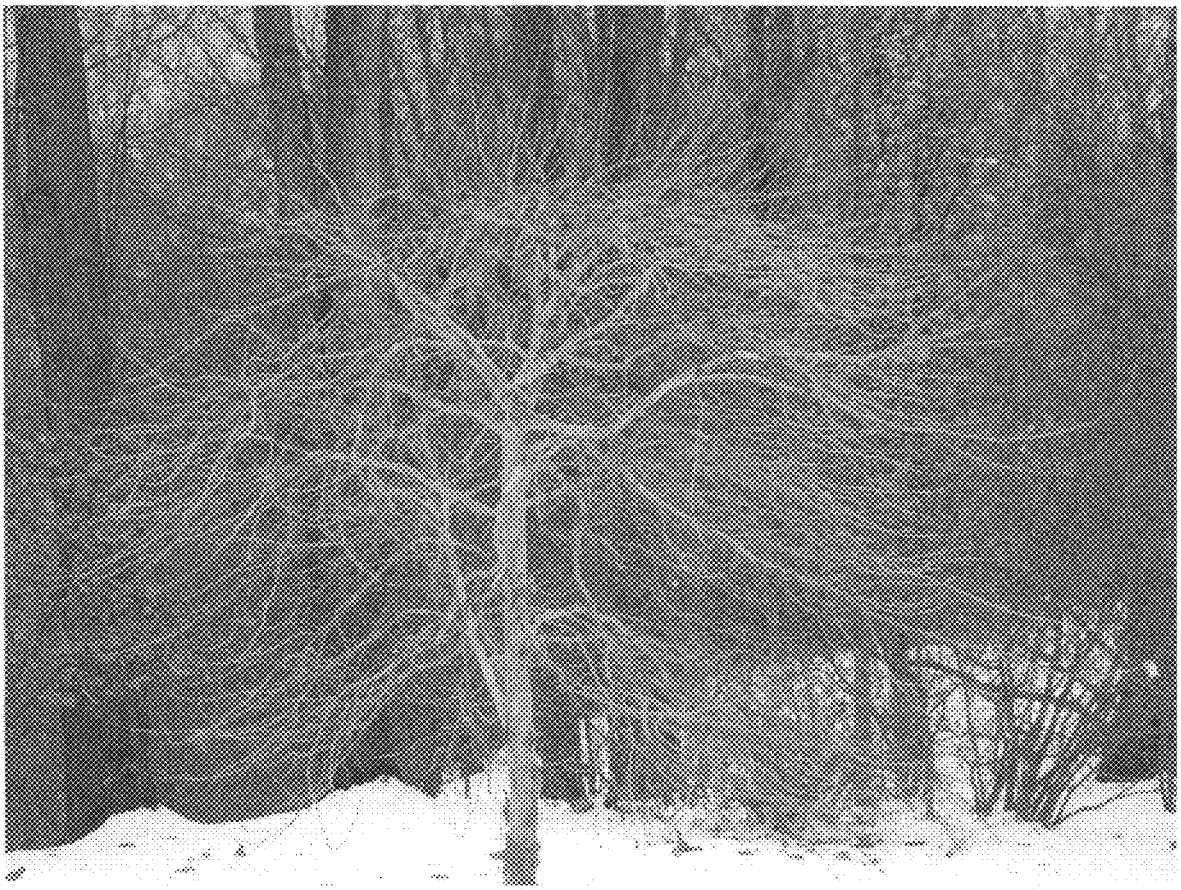
FIG. 1, illustrates the overall appearance of 'DRABROT' showing the semi-weeping and contorted growth habit, and the exfoliating bark patches, as exhibited on a 17-year old dormant, leaf-free specimen in a landscape application.
Figure 2:
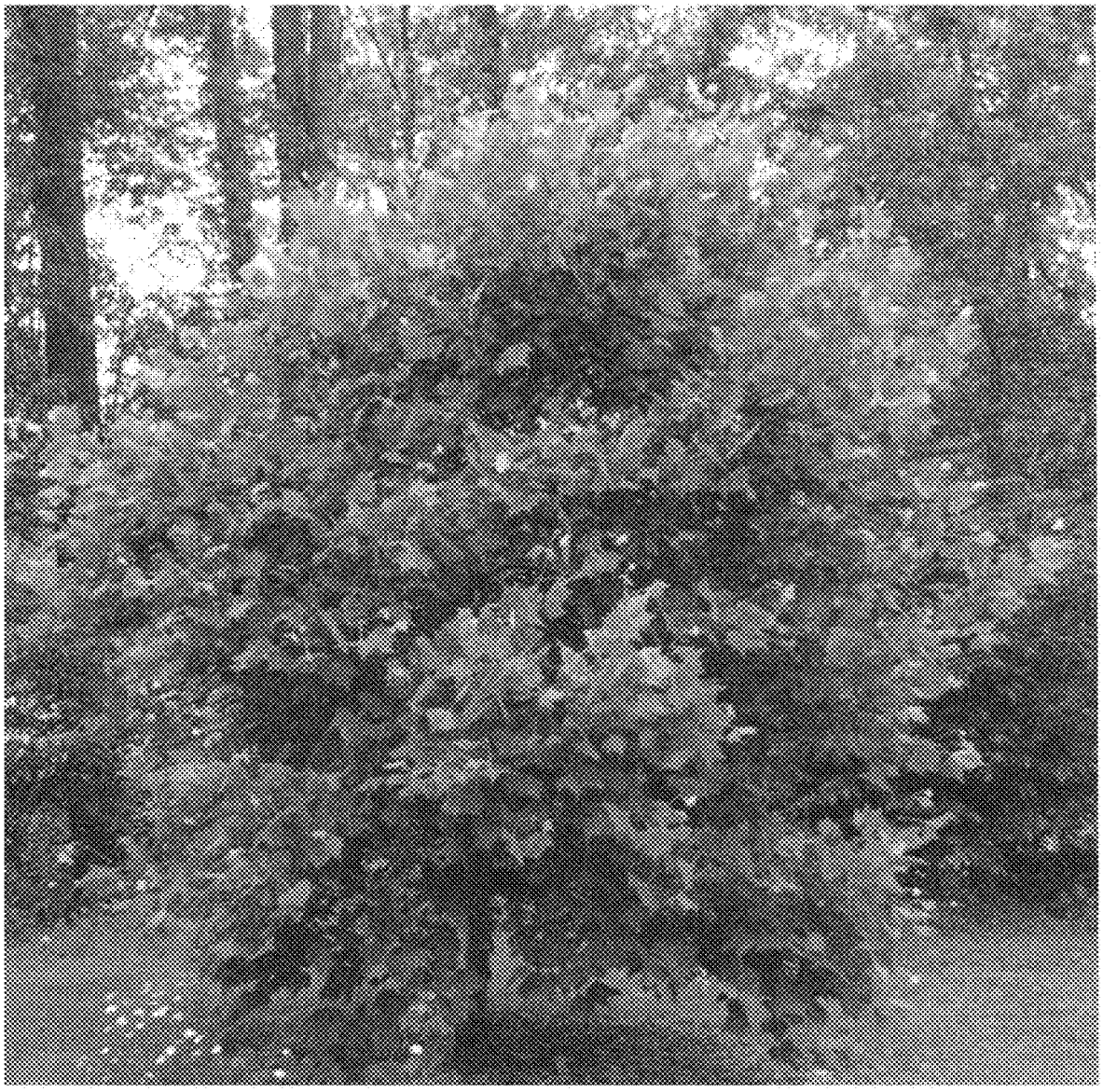
FIG. 2, illustrates the overall appearance of 'DRABROT' in mid-summer, showing the dense habit and dark green, disease-free leaves, as exhibited on a 17-year old specimen in a landscape application.

The invention claimed is:

1. A new and distinct variety of *Platanus occidentalis* named 'DRABROT', substantially as described and illustrated herein.

* * * * *